(12) United States Patent
Henseler et al.

(10) Patent No.: US 9,091,771 B2
(45) Date of Patent: Jul. 28, 2015

(54) SYSTEM AND METHOD FOR IMPROVING DETECTION OF GAMMA INTERACTIONS IN A POSITRON EMISSION TOMOGRAPHY SYSTEM

(75) Inventors: Debora Henseler, Erlangen (DE); Ronald Grazioso, Knoxville, TN (US); Nan Zhang, Knoxville, TN (US); Matthias J. Schmand, Lenoir City, TN (US); Sanghee Cho, Knoxville, TN (US)

(73) Assignees: Siemens Aktiengesellschaft, Munich (DE); Siemens Medical Solutions USA, Inc., Malvern, PA (US)

( * ) Notice: Subject to any disclaimer, the term of this patent is extended or adjusted under 35 U.S.C. 154(b) by 635 days.

(21) Appl. No.: 13/539,915

(22) Filed: Jul. 2, 2012

(65) Prior Publication Data

US 2013/0009063 A1    Jan. 10, 2013

Related U.S. Application Data

(60) Provisional application No. 61/505,161, filed on Jul. 7, 2011.

(51) Int. Cl.
*G01T 1/29* (2006.01)
*A61B 6/03* (2006.01)
*G01T 1/00* (2006.01)
*A61B 6/00* (2006.01)

(52) U.S. Cl.
CPC ............... *G01T 1/2985* (2013.01); *A61B 6/037* (2013.01); *A61B 6/00* (2013.01); *G01T 1/00* (2013.01)

(58) Field of Classification Search
CPC ........... G01T 1/00; G01T 1/2985; A61K 6/00
USPC ............................................. 250/362, 363.03
See application file for complete search history.

(56) References Cited

U.S. PATENT DOCUMENTS

2005/0253073 A1* 11/2005 Joram et al. .............. 250/363.03
2005/0253074 A1* 11/2005 Jones et al. .............. 250/363.04
2012/0153165 A1*  6/2012 Ott ................................ 250/362

* cited by examiner

*Primary Examiner* — David Porta
*Assistant Examiner* — Meenakshi Sahu
(74) *Attorney, Agent, or Firm* — Peter Kendall

(57) ABSTRACT

A system and method are provided for determining the onset of gamma interactions for positron emission tomography (PET) imaging more accurately than with existing techniques. The timing of a sequence of primary trigger events is obtained and used to determine a weighted combination, which mixes the timing information from the various primary trigger events to compute an overall event trigger timing with improved time resolution. Numerical simulations demonstrate that the invention improves time resolution by approximately 10% over state-of-the-art methods. This improved time resolution directly benefits the imaging performance of the PET scanner, especially in time-of-flight (TOF) mode, where a high time resolution directly translates to a reduction in image noise at the same dose—or, alternatively, a reduction of dose to the patient or scan time for the same image quality.

21 Claims, 8 Drawing Sheets

SYSTEM AND METHOD FOR IMPROVING DETECTION OF GAMMA INTERACTIONS IN A POSITRON EMISSION TOMOGRAPHY SYSTEM

CROSS-REFERENCE TO RELATED APPLICATIONS

This application claims the benefit of U.S. Provisional Patent Application 61/505,161, filed on Jul. 7, 2011, the entire disclosure of which is hereby incorporated by reference.

FIELD

The invention generally relates to nuclear medicine and systems for obtaining nuclear medicine images. In particular, the invention relates to systems and methods for accurately determining the onset of gamma interactions for positron emission tomography (PET) imaging.

BACKGROUND

Medical radionuclide imaging, commonly referred to as nuclear medicine, is a unique specialty wherein ionizing radiation is used to acquire images which show the function and anatomy of organs, bones or tissues of the body. The technique of acquiring nuclear medicine images entails first introducing biologically appropriate radiopharmaceuticals into the body—typically by injection, inhalation, or ingestion. These radiopharmaceuticals are attracted to specific organs, bones or tissues of interest (These exemplary organs, bones, or tissues are also more generally referred to herein using the term "objects"). Upon arriving at their specified area of interest, the radiopharmaceuticals produce gamma photon emissions which emanate from the body and are then captured by a scintillation crystal. The interaction of the gamma photons with the scintillation crystal produces flashes of light which are referred to as "events." Events are detected by an array of photodetectors (such as photomultiplier tubes) and their spatial locations or positions are then calculated and stored. In this way, an image of the organ or tissue under study is created from detection of the distribution of the radioisotopes in the body. Known applications of nuclear medicine include: analysis of kidney function, imaging blood-flow and heart function, scanning lungs for respiratory performance, identification of gallbladder blockage, bone evaluation, determining the presence and/or spread of cancer, identification of bowel bleeding, evaluating brain activity, locating the presence of infection, and measuring thyroid function and activity. Hence, accurate detection is vital in such medical applications.

One particular nuclear medicine imaging technique is known as positron emission tomography, or PET. Positron emission tomography is used to produce images for diagnosing the biochemistry or physiology of a specific organ, tumor or other metabolically active site. The measurement of tissue concentration using a positron emitting radionuclide is based on coincidence detection of the two gamma photons arising from a positron annihilation. When a positron is annihilated by an electron, two 511 keV gamma photons are simultaneously produced and travel in approximately opposite directions. Gamma photons produced by an annihilation event can be detected by a pair of oppositely disposed radiation detectors capable of producing a signal in response to the interaction of the gamma photons with a scintillation crystal. Annihilation events are typically identified by a time coincidence between the detection of the two 511 keV gamma photons in the two oppositely disposed detectors; i.e., the gamma photon emissions are detected virtually simultaneously by each detector. When two oppositely disposed gamma photons each strike an oppositely disposed detector to produce a time coincidence event, they also identify a line-of-response (LOR) along which the annihilation event has occurred.

After being sorted into parallel projections, the LOR defined by the coincidence events are used to reconstruct a three-dimensional distribution of the positron-emitting radionuclide within the patient. In two-dimensional PET, each 2D transverse section or "slice" of the radionuclide distribution is reconstructed independently of adjacent sections. In fully three-dimensional PET, the data are sorted into sets of LOR, where each set is parallel to a particular detector angle, and therefore represents a two dimensional parallel projection $p(s, \phi)$ of the three dimensional radionuclide distribution within the patient—where "s" corresponds to the distance of the LOR from the center of the detector and "$\phi$" corresponds to the angle of the detector plane with respect to the x axis in (x, y) coordinate space (in other words, $\phi$ corresponds to a particular LOR direction).

Coincidence events are integrated or collected for each LOR and stored in a sinogram. In this format, a single fixed point in f(x, y) traces a sinusoid in the sinogram. In each sinogram, there is one row containing the LOR for a particular azimuthal angle $\phi$; each such row corresponds to a one-dimensional parallel projection of the tracer distribution at a different coordinate along the scanner axis. This is shown conceptually in FIG. 1.

An event is registered if both crystals detect an annihilation photon within a coincidence time window $\tau$ (e.g., on the order of 4-5 nsec), depending on the timing properties of the scintillator and the field of view (FOV). The FOV is defined as the volume between the detectors; and a pair of detectors is sensitive only to coincidence events occurring in the FOV. Therefore, the need for physical collimation is eliminated and sensitivity is significantly increased. Accurate corrections (for example, attenuation correction) can be made for the self-absorption of photons within the patient so that accurate measurements of tracer concentration can be made.

The number of time coincidences detected per second within a FOV of a detector is the count rate of the detector. The count rate at each of two oppositely disposed detectors, A and B, can be referred to as singles counts or $S_A$ and $S_B$, respectively. The time required for a gamma photon to travel from its point of origin to a point of detection is referred to as the time-of-flight (TOF) of the gamma photon. TOF is dependent upon the speed of light c and the distance traveled. A time coincidence or coincidence event is identified if the time difference between the arrivals of signals in a pair of oppositely disposed detectors is within the coincidence time window $\tau$. In conventional PET, the coincidence detection time window $\tau$ is wide enough so that an annihilation event occurring anywhere within the object will produce annihilation gamma photons reaching their respective detectors within the coincidence window. Coincidence time windows of 4.5-12 nsec are common for conventional PET, and are largely determined by the time resolution capabilities of the detectors and electronics.

As illustrated in FIG. 2, if an annihilation event occurs at the midpoint of a LOR, the TOF of the gamma photon detected in detector A ($T_A$) is equal to the TOF of the gamma photon detected in detector B ($T_B$). If an annihilation event occurs at a distance $\Delta x$ from the midpoint of the LOR, the difference between $T_A$ and $T_B$ is $\Delta t = 2\Delta x/c$, where c is the speed of light. If d is the distance between detectors, the TOF difference Δt could take any value from −d/c to +d/c, depending on the location of the annihilation event.

Time-of-flight (TOF) positron emission tomography (PET) ("TOF-PET") is based on the measurement of the difference Δt between the detection times of the two gamma photons arising from the positron annihilation event. This measurement allows the annihilation event to be localized along the LOR with a resolution of about 75-120 mm FWHM, assuming a time resolution of 500-800 ps (picoseconds). Though less accurate than the spatial resolution of the scanner, this approximate localization is effective in reducing the random coincidence rate and in improving both the stability of the reconstruction and the signal-to-noise ratio (SNR), especially when imaging large objects. Thus, in TOF-PET, the "TOF" coordinate, Δt, is stored together with s and φ.

One task of a good PET detector is to measure the time stamp of the gamma interaction in the detector (usually within the scintillator) as accurately as possible. The required accuracy of a few hundred ps (picoseconds) is on a much shorter time scale than the width or duration of the photon emission and also, normally, the width of the pulse from the photosensor for a single photon. The figure of merit is the coincidence time resolution, which is defined as the full width half maximum (FWHM) of the measured trigger time difference between two detectors, when detecting the signal from a fixed point source positron emitter between them.

Time resolution is a measure of the uncertainty of the measured time difference Δt between the two detections. The time resolution is used in the reconstruction algorithm as a kernel for a localization probability function. The events are located along the LOR identified by the two detectors; its most probable position is set to the position corresponding to the measured TOF difference t.

There are various types of photosensors that are used or have been studied for use in PET scanners: most commercial systems today are based on photomultiplier tubes (PMTs), which detect the light emitted by a scintillator following a gamma event and convert detected light photons into electrical signals. Some recent systems and scanner prototypes have used avalanche photodiodes (APDs) to detect the gamma event. Silicon photomultipliers (SiPMs) seem to be a promising sensor type for future detector generations, because they combine some advantages of PMTs (high signal gain and high speed) with those of APDs (small form factor and compatibility with magnetic fields).

SiPMs offer some of the best time resolutions among existing photosensor devices, and in particular are very suitable for detecting the scintillation light from Lutetium Oxyorthosilicate (LSO) and other typical PET scintillators. Coincidence time resolution values in the range of 150 to 500 ps have been obtained for different sensor types and different coupling configurations, demonstrating the feasibility of this technology for TOF-PET. The best timing resolution is usually achieved by coupling each single LSO crystal with typical dimensions of 3×3×20 mm$^3$ to a single sensor pixel, which is matched to the 3×3 mm$^2$ light extraction face.

Analog SiPMs consist of an array of Geiger-mode APDs (or microcells) connected in parallel to form a two-terminal device. Then, although the state of the individual microcell can be described as digital (ON or OFF), the overall output becomes an analog signal, which is roughly proportional to the amount of incident light.

One very recent development in this field is the so-called digital SiPM (dSiPM) technology by Philips (see, e.g., WO2009/019660 A2). This sensor design achieves a high signal-to-noise ratio and an excellent time resolution by integrating CMOS electronics on the same wafer as the SiPM sensor and digitizing the signal of each Geiger-mode APD cell. In contrast to the analog sensors discussed above, the dSiPM can directly measure the trigger time for the first, second, third, . . . avalanche, thus giving measured arrival times for the first few measured photons. Setting the trigger on the first photon has been shown to give the best timing results for any SiPM so far (T. Frach et al., "Digital Silicon Photomultiplier—Principle of Operation and Intrinsic Detector Performance," IEEE Nuclear Science Symposium, Talk 28-5, 2009). It has been shown theoretically that the first few photons from the emission statistics carry the most precise information about the time of the original event interaction (Y. Shao, "A new timing model for calculating the intrinsic timing resolution of a scintillator detector," Phys. Med. Biol. 52 (2007) 1103-1117).

Increasing the accuracy of the trigger time for detecting the onset of a gamma interaction event is especially important for time-of-flight PET (TOF-PET), where the variance in the reconstructed image is reduced by using the additional spatial information from the trigger time differences of the two opposite detectors that measure the same positron decay (W. Moses, IEEE Trans. Nucl. Sci. vol NS-50, p. 1325-1330, 2003).

In time-of-flight PET, the noise equivalent count rate (a measure of the detected counts corrected for the noise contribution of scatter and random coincidences; in other words, a measure of the effective sensitivity of the PET scanner) is inversely proportional to the time resolution of the PET scanner. Thus, improving the time resolution is the key for better performing TOF-PET scanners. Table 1 illustrates the time resolution, spatial uncertainty, and estimated TOF noise equivalent count rate (NEC) gain for a 40 cm diameter uniform cylinder (M. Conti, "State of the art and challenges of time-of-flight PET," Physica Medica 25: 1, p. 5, 2008).

TABLE 1

Effects of Improved Time Resolution

| Time resolution (ns) | Δx (cm) | TOF NEC gain |
|---|---|---|
| 0.1 | 1.5 | 26.7 |
| 0.3 | 4.5 | 8.9 |
| 0.5 | 7.5 | 5.5 |
| 1.2 | 18.0 | 2.2 |

SUMMARY

The invention provides a method for improving the accuracy of timing information data received from the photosensors by combining them in a weighted combination. By mixing the timing information from the first trigger event with information from subsequent trigger events, the time resolution of the overall event trigger timing can be improved.

According to one aspect of the invention, a method for detecting the onset of a gamma interaction for positron emission tomography (PET) imaging is disclosed in which a sequence of primary trigger event timings is received, and weights are determined for each of the primary trigger event timings, the weight for the first primary trigger event timing in the sequence being the largest. In particular embodiments of the invention, the weights decrease for each subsequent primary trigger event timing in the sequence. In particular embodiments of the invention, where the sequence contains at least three primary trigger event timings, the weight for the last primary trigger event timing will be greater than the weight for at least one other primary trigger event timing in the sequence. The onset of a gamma interaction is determined based on at least an overall event trigger timing, which is based on a weighted combination of the primary trigger event timings and their corresponding weights.

Certain embodiments of the invention use a weighted linear combination to mix the timing information of multiple trigger events. The weights of the weighted linear combination can be modified iteratively until the time resolution achieves a predetermined threshold value. The weighted combination may also be of higher order, for example, quadratic or cubic. The weights can be determined by evaluating the time resolution for a plurality of test weights in a numerical simulation, or in an experimental setup. The weights can also be modified iteratively during PET imaging, in order to improve time resolution during operation.

Other aspects of the invention include a gamma interaction detection system for positron emission tomography (PET) imaging, comprising a data acquisition system operable to receive a sequence of a plurality of primary trigger event timings, a processor, and a computer-readable medium comprising instructions executed by the processor to implement the methods and processes described herein.

In another aspect of the invention, a computer-readable non-transitory storage medium comprises computer-readable program instructions representative of the steps of the methods and processes described herein.

DETAILED DESCRIPTION

The invention will now be described and disclosed in greater detail. It is to be understood, however, that the disclosed embodiments are merely exemplary of the invention and that the invention may be embodied in various and alternative forms. Therefore, specific structural and functional details disclosed herein are not to be interpreted as limiting the scope of the claims, but are merely provided as an example to teach one having ordinary skill in the art to make and use the invention.

Two methods are commonly used with analog photosensors to derive an event trigger: the constant fraction discriminator (CFD) and the leading edge (LE) trigger. Leading-edge triggers are well suited to photosensors with short pulse responses and for setups with low electronics noise, so that the trigger level can be set very low, to trigger on the first few photons from the scintillator emission (R. Vinke et al., "Optimizing timing resolution of SiPM sensors for use in TOF-PET detectors," NDIP08 Conference Talk). Based on the theoretical findings of Shao, detectors should use a leading-edge trigger set extremely low—low enough to trigger on the first emitted photon.

In practice, however, there are limits to how low the trigger level can be set, due to the presence of random dark events of the microcells and other noise sources, such as amplifier noise. If the trigger level is so low that such noise can cause false triggers, then an event verification scheme must be used to discard the irrelevant data. But, it takes time to perform these verifications before the data acquisition is ready for the next event, so a very low trigger level setting will lead to a substantial fraction of detector dead time and reduced performance. This detector dead time is typically on the scale of 10's of nanoseconds, leading to a significant probability of missing the next event.

Figure 1:
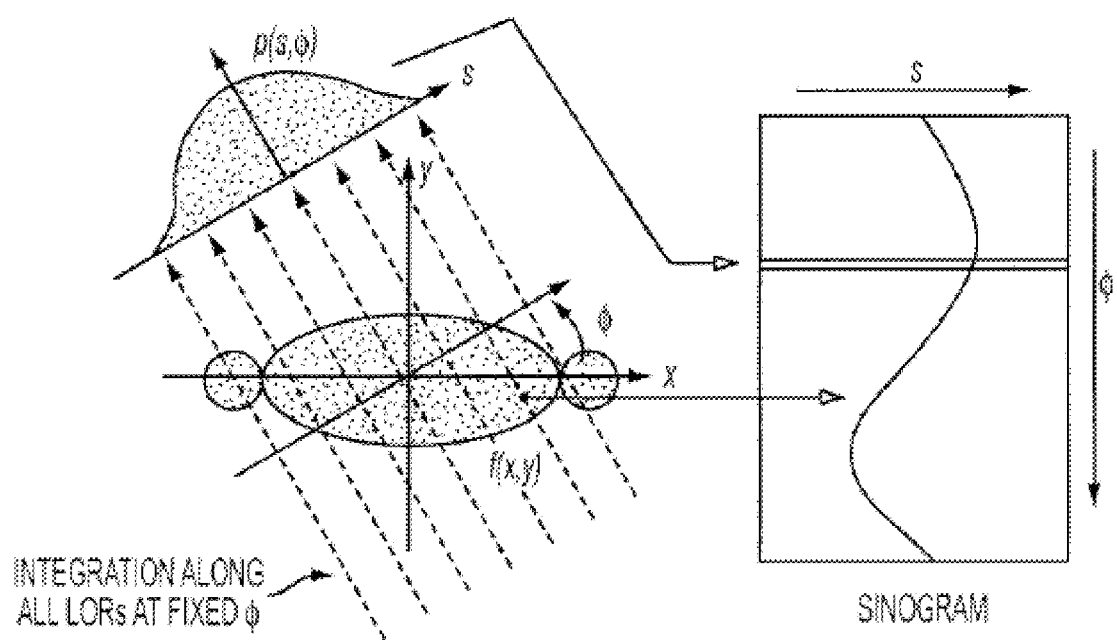
FIG. 1 is a diagram illustrating the relationship between PET projection data and a sinogram.
Figure 2:
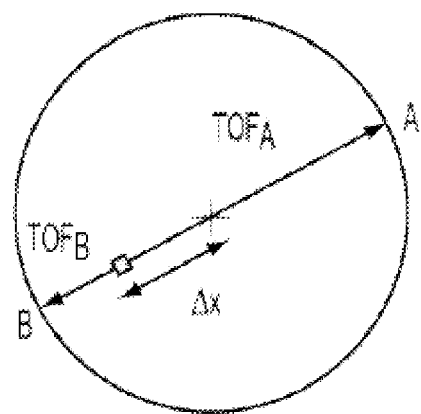
FIG. 2 is a diagram illustrating the concept of time of flight in PET imaging.
Figure 3:
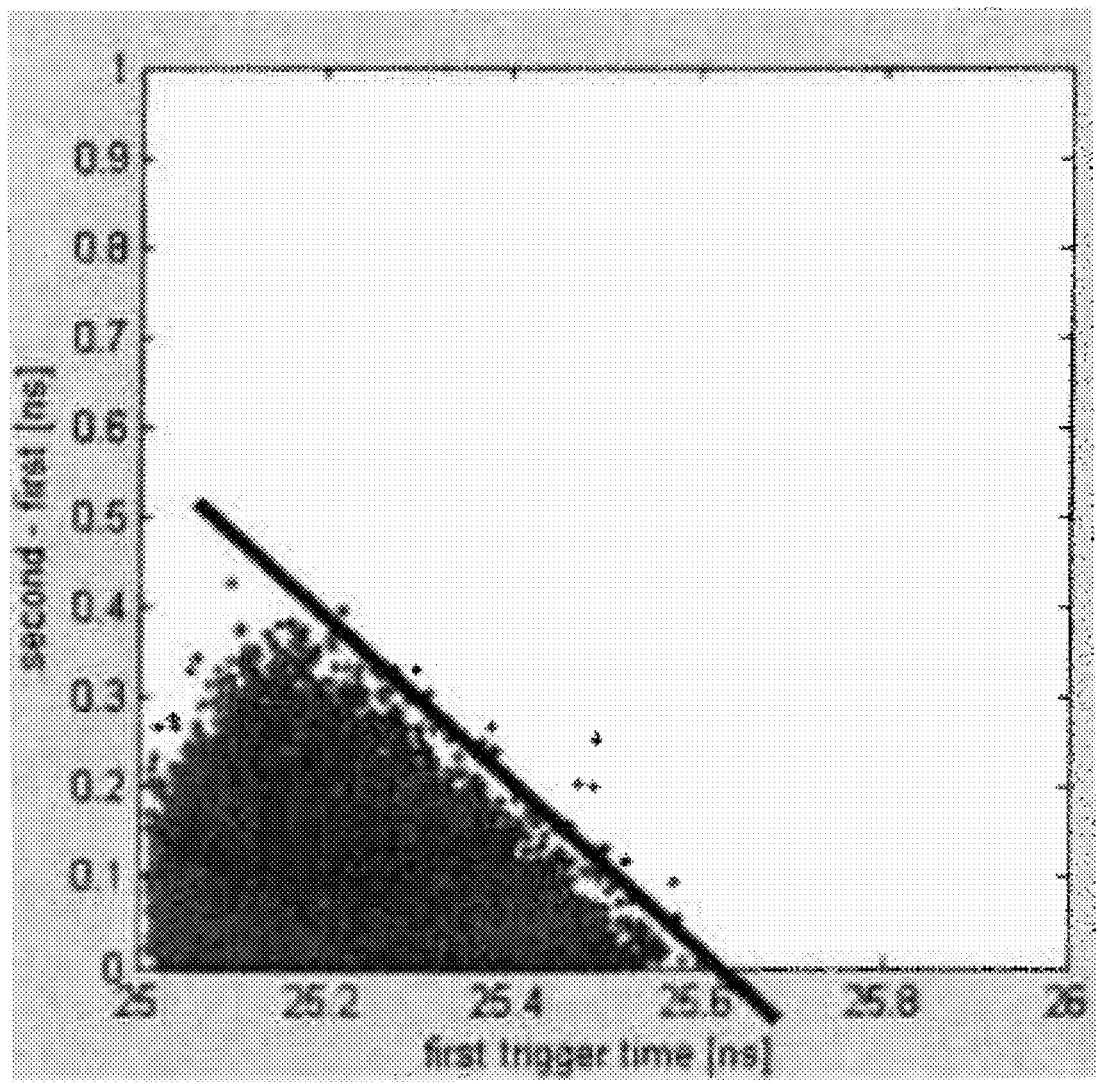
FIG. 3 is a graph illustrating the correlation between the arrival time of the first photon and further photons in the statistical distribution.

Instead of triggering only on one very low trigger level, the various embodiments of the invention achieve improved time resolution by combining a sequence of multiple trigger events to determine an overall trigger event timing. The additional timing information that can be gained from using more than one trigger lies in the correlation between the arrival time of the first photon and further photons in the statistical distribution. FIG. 3 illustrates the correlation between the first event trigger and the time delay between the first and second trigger events for a few thousand runs of a numerical model. The bar highlights the correlation: the late time stamps for the first avalanche trigger tend to correspond to a small distance between the first and second trigger.

Figure 4:
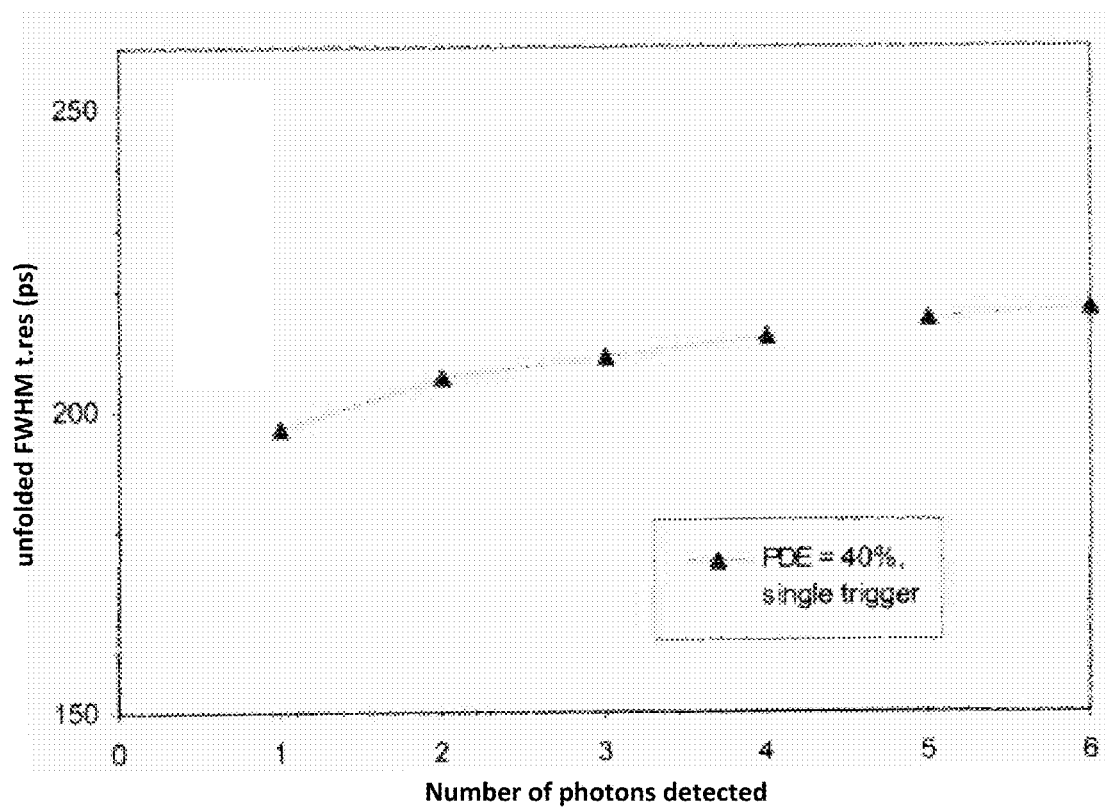
FIG. 4 is a graph illustrating the simulated time resolution where the event trigger is set to the time of various detected photons.

In the various embodiments of the invention, this correlation indicates that additional timing precision could be gained if information from subsequent triggers is used, in addition to the first trigger (which by itself is the most accurate of the single triggers, as seen in FIG. 4). For example, by mixing in some part of the second trigger, the "late" tail in the distribution of the first trigger can be somewhat reduced. The information from several triggers is mixed together to generate the overall event trigger from a weighted combination of a sequence of several primary event triggers, because in this way no arbitrary time shifts are introduced.

Thus, even though the theoretical best timing information comes from the first pair of photoelectrons emitted from a gamma interaction, the measured timing information from any particular pair of electrons also contains other, "noisy" information, for example, the effects of scintillator rise time and optical path length, timing delays and jitter from the electronic components (such as digitizers), and so on. The various embodiments of the invention reduce the effects of this "noisy" information on the time resolution of the calculated timing by combining the timing information from multiple primary event triggers (corresponding to multiple emitted photons). As a result, the various embodiments of the invention improve the time resolution of the overall measured timing information.

Various embodiments of the invention use a numerical model, which takes into account the scintillator quantum statistics, its temporal emission distribution and the delays from optical path lengths within the scintillator up to reaching the sensor surface. The model uses a 3×3×20 mm$^3$ Lutetium Oxyorthosilicate (LSO) crystal. The output from the simulation model is the "unfolded full width half magnitude (FWHM) time resolution," which is the contribution from just a single detector and can be converted to the coincidence time resolution by multiplying with a factor sqrt(2).

The time resolution of a PET imaging system is directly related to the imaging performance of the PET scanner, especially in time-of-flight (TOF) mode. In the various embodiments of the invention, improved time resolution directly translates to a reduction in image noise at the same dose—or, alternatively, a reduction of dose to the patient or scan time for the same image quality. In particular embodiments of the invention, improved TOF performance is also useful to reduce image artifacts, especially in limited transaxial angle coverage applications (such as a dedicated breast TOF-PET scanner), and for high resolution studies (which are stymied by limited acquisition times).

Figure 5:
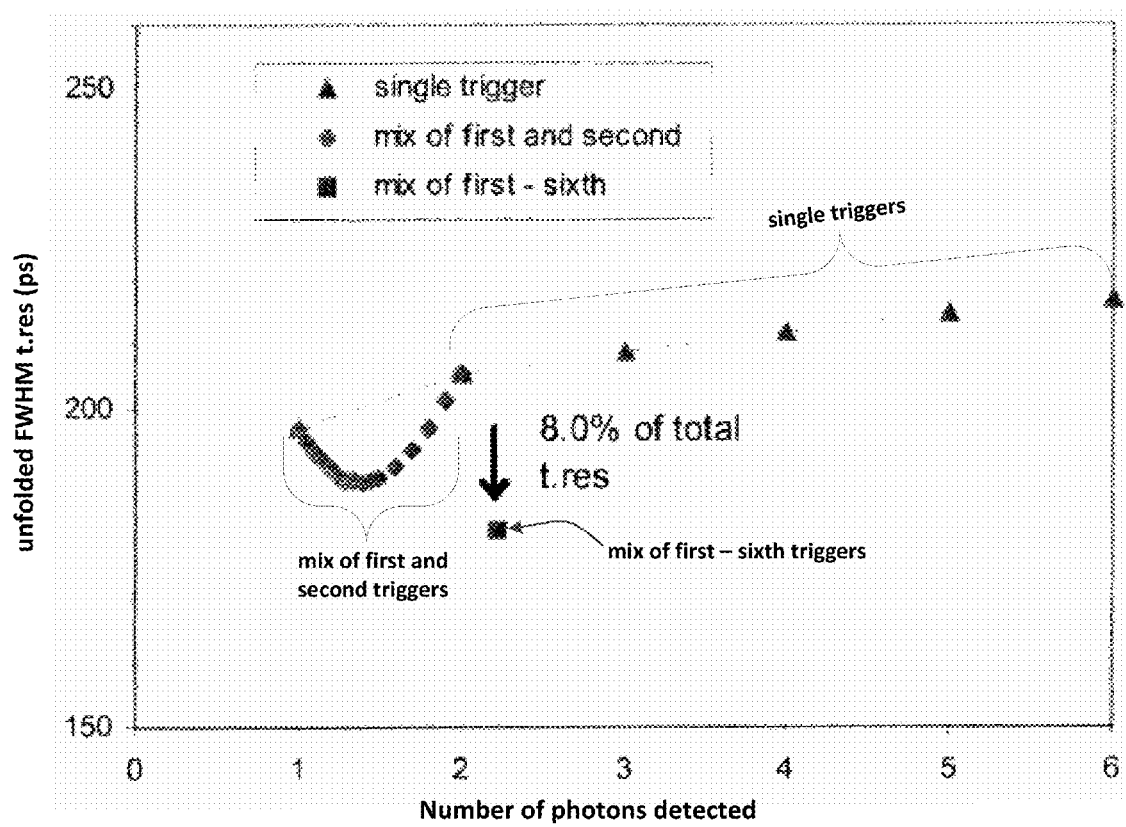
FIG. 5 is a graph illustrating the additional timing precision gained by mixing in information from subsequent triggers.

In an exemplary embodiment of the invention, visible photons from the scintillator are detected by avalanche triggers in a digital SiPM. The digital SiPM assigns timestamps to each visible photon detected, which represent the primary trigger event timings for each photon. The primary event trigger timings are then combined in a weighted combination. In particular embodiments of the invention, the multiple event trigger timings are combined in a weighted linear combination. The triangle-shaped data points in FIGS. 4 and 5 show the time resolution for each of the first six triggers, considered separately. The diamond-shaped data points in FIG. 5 show the improvement in time resolution that is predicted by the numerical simulation for a series of linear combinations of the first and second trigger, with varying weights. In one embodiment of the invention, a 4.3% improvement in time resolution is obtained for a combination of 60% of the first trigger and 40% of the second trigger.

The various embodiments of the invention achieve even larger improvements in time resolution by using more than just the first two triggers: the square-shaped data point in FIG. 5 shows the best linear combination of the first through sixth triggers, which was found numerically to give the best time resolution for a large ensemble of simulated emission pulses, with a statistical distribution of emission times and also optical path lengths.

In one embodiment, the overall trigger time $t_{event}$ is formed from the individual six triggers ($t_1$-$t_6$) by the following linear combination:

$$t_{event} = 0.56*t_1 + 0.10*t_2 + 0.08*t_3 + 0.06*t_4 + 0.04*t_5 + 0.14*t_6$$

The first primary event trigger $t_1$ carries the largest weight, which correlates with the fact that, by itself, it gives the best time resolution of the six triggers. But, the summed weights of the other five components form almost half of the total. Also, the weight of the sixth trigger component is increased to be slightly higher than the preceding one, to compensate for the effect of truncating the sequence at this point.

The various embodiments of the invention may include an even larger number of triggers, which lead to further, incremental improvements in the time resolution, but additional triggers do trade-off with increased read-out and processing requirements and increased noise. The number of possible triggers varies based on the different types of photosensors: an SiPD, for example, might detect around 300-400 photons per gamma interaction. Any number of triggers could be combined to determine an overall trigger time, for example, anywhere from 2 to 100 triggers could be used. It has been determined that good results are found using between 2 and 20 triggers, with even better results using a smaller range of 2 to 6 triggers, due to the diminishing returns of additional triggers and the increased processing load for larger combinations.

In particular embodiments of the invention, the weights for the primary trigger event timings in the weighted combination are determined by numerically simulating gamma interaction in a positron emission tomography (PET) system, and analyzing the results for various possible choices of test weights to determine which test weights achieve the desired time resolution for the overall trigger event timing. See, for example, the diamond-shaped data points in FIG. 5, which represent the simulated time resolution for various combinations of the first and second primary event trigger timings. The optimized time resolution found by this numerical simulation was for a weight of 60% for the first primary event trigger timing, and 40% for the second primary event trigger timing, resulting in a 4.3% improvement in time resolution over use of the first primary event trigger timing alone. The time resolution could also be measured by an experimental setup, instead of a numerical simulation, wherein experimental data regarding gamma interaction in a positron emission tomography (PET) system could be analyzed for various possible choices of test weights to determine which test weights achieve the desired time resolution for the overall trigger event timing. The weights could also be determined in other ways, such as by iteratively modifying the weights while the process is ongoing. For example, during operation of a system, the time resolution could be evaluated, and the weights could be modified until the time resolution meets certain criteria, e.g., the time resolution for the overall event trigger timing achieves a predetermined threshold value desirable for the particular implementation (for instance, less than 1 nanosecond, less than 500 picoseconds, less than 200 picoseconds, less than 100 picoseconds, or any other threshold value). The weights could also be modified iteratively during operation of the system, for example, the weights could be adjusted manually while viewing the output of a PET imaging system, until the image clarity improves to a desirable level (e.g., few artifacts are seen, or the outlines of a tumor become clearly visible, etc.).

Further simulations with different scintillator properties show that the amount of information gained by the various embodiments of the invention is larger for longer rise times of the scintillator: for a rise time constant of 500 ps, the best linear combination of the first six triggers leads to a greater than 10% improvement in time resolution, compared to using just the first trigger. Similarly, other parameters like the crystal geometry and the resulting optical path length differences would also affect the expected gains from this method.

In particular embodiments of the invention, timing information is obtained from a digital SiPM, where digital time stamps can be directly obtained for the first, second, . . . etc. detected photons. For this case, an improvement in time resolution of approximately 10% is predicted by numerical simulations.

Figure 6:
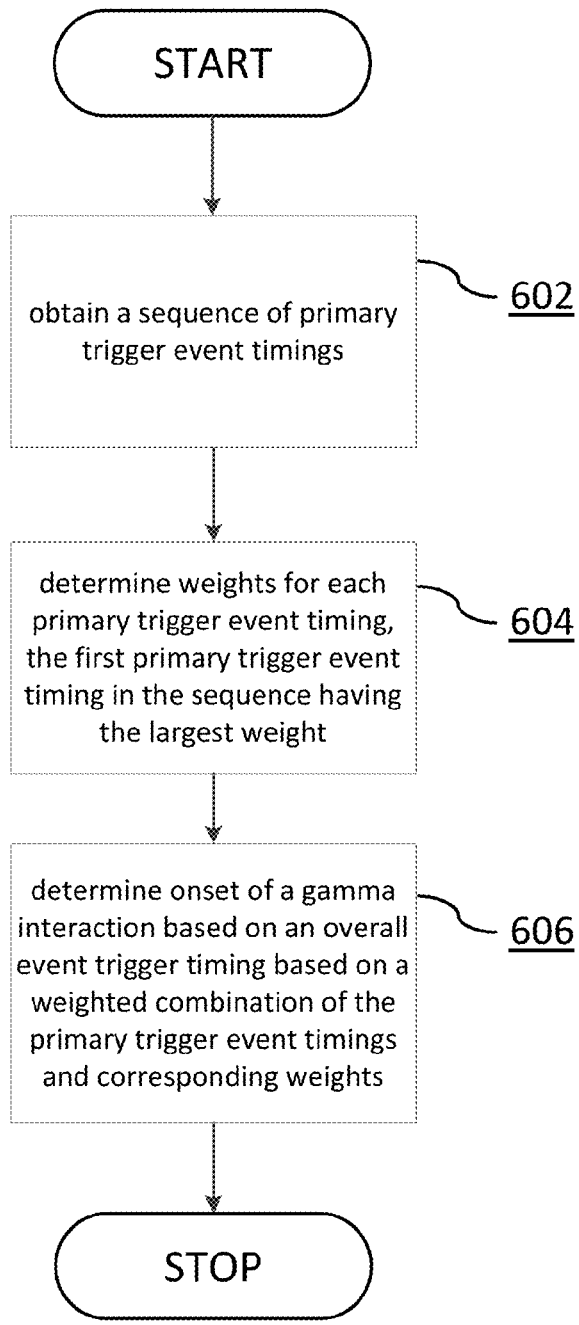
FIG. 6 is a flow diagram illustrating an embodiment of the method of the invention for determining the onset of a gamma interaction event with improved accuracy.

In an exemplary embodiment of the invention, illustrated in FIG. 6, a sequence of primary trigger event timings (e.g., digital timestamps from dSiPM sensors) are obtained in step 602. Weights are determined for each of the primary trigger event timings in step 604. The weight for the first primary trigger event timing in the sequence is the largest, because it carries the best timing information of the individual primary event triggers. In particular embodiments, the weights decrease for each subsequent primary trigger event timing in the sequence. In particular embodiments, where the sequence contains at least three primary trigger event timings, then the weight for the last primary trigger event timing will be greater than the weight for at least one other primary trigger event timing in the sequence, in order to compensate for the effect of cutting the sequence off at that point. In step 606, the onset of a gamma interaction is determined based on at least an overall event trigger timing, which is based on a weighted combination of the primary trigger event timings and their corresponding weights.

Figure 7:
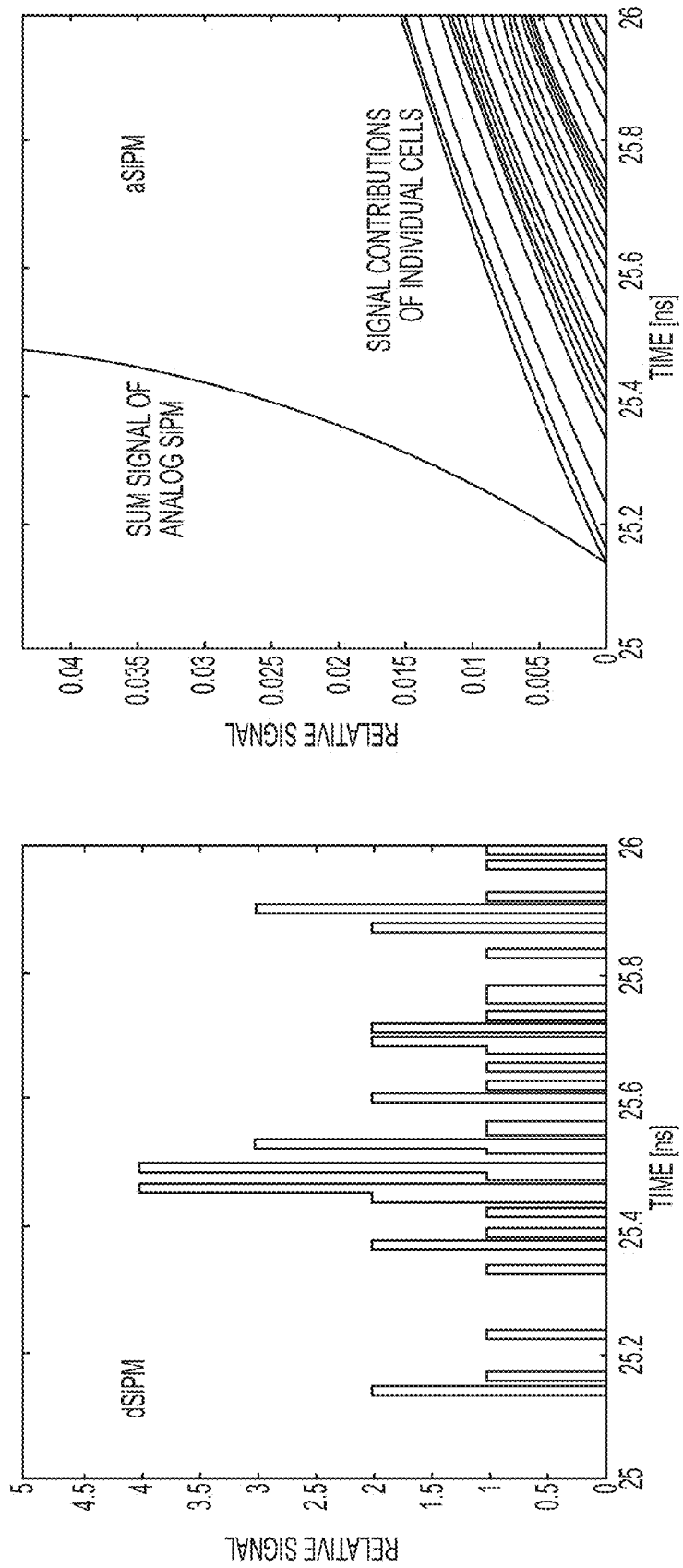
FIG. 7 is a schematic plot illustrating the difference between analog and digital time stamps due to the convolution of photon arrival time with the pulse shape of the sensor response.

The various embodiments of the invention can also be used to improve the time resolution of other types of sensors (e.g., PMTs or APDs, either analog or digital). In particular embodiments of the invention, two or more "primary triggers" (e.g., without limitation, leading-edge thresholds, or constant-fraction discriminators) are combined into a weighted combination. The greatest improvement in time resolution occurs where the rise time of the scintillator and/or the spread of optical path lengths in the crystal has a significant contribution to the overall signal pulse shape, as shown in FIG. 7, which illustrates the difference between the digital trigger time stamps in a dSiPM and the signal output of an analog device, due to the convolution of photon arrival time with the temporal response characteristic of the photosensor and possible further broadening by the front-end electronics. In those cases, the summed, analog signal would have the steepest slope not at the very beginning of the pulse, but at a slightly later point in time, where the next few photons arrive. It therefore improves the time resolution to mix in the timing information of the next few photons with the timing trigger of the first photon detected.

Figure 8:
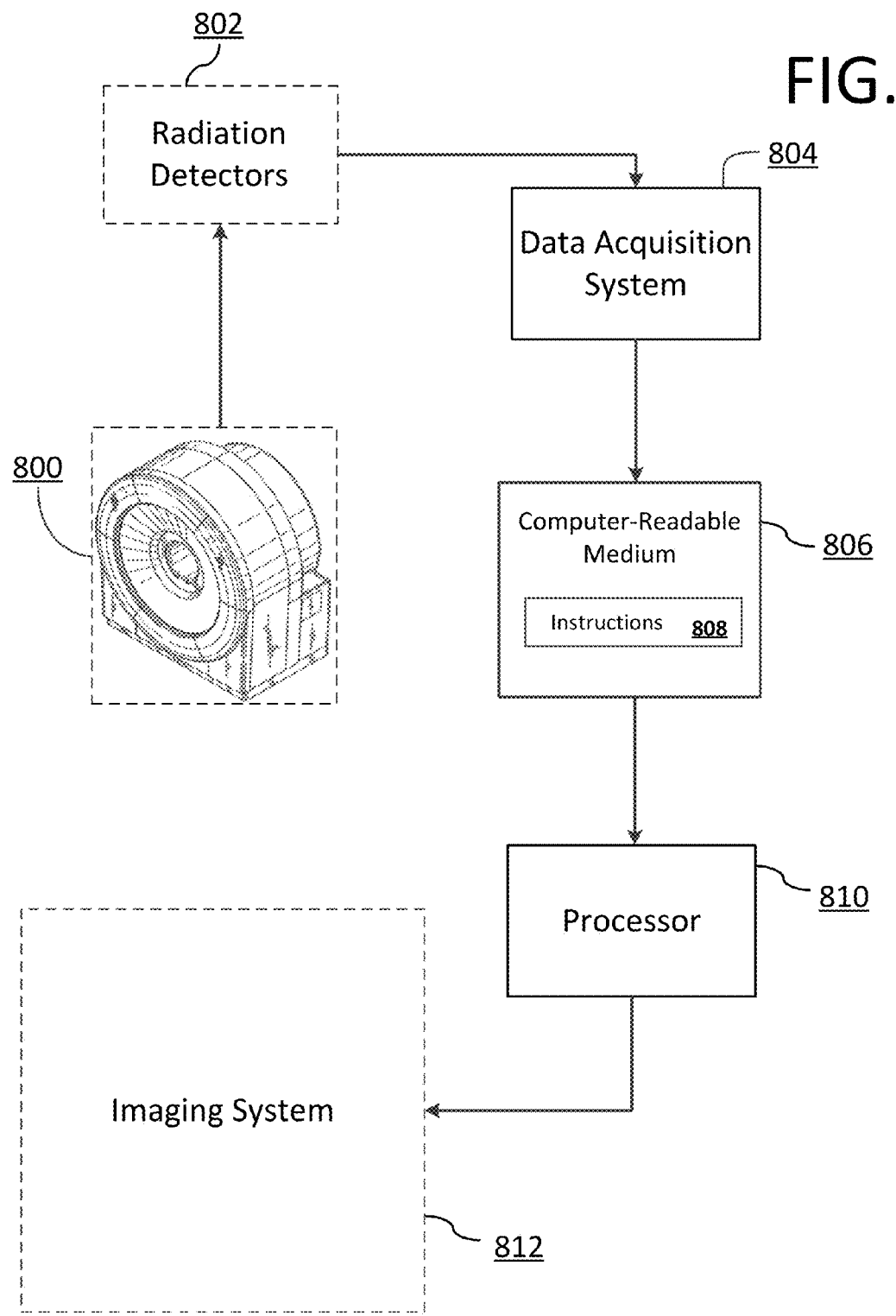
FIG. 8 is a block diagram illustrating an embodiment of a system suitable for implementing the methods and processes described herein.

FIG. 8 illustrates an exemplary implementation of the invention in a PET imaging system. Gamma interactions occur in the PET scanner 800, and the resulting gamma photons are detected by radiation detectors 802. These radiation detectors are preferably scintillators coupled to photosensors. The photosensors are preferably digital silicon photodiodes (dSiPDs), but can be any type of sensor used in PET imaging; for example, without limitation, photomultipliers (PMTs), avalanche photodiodes (APDs), or silicon photodiodes (SiPDs), any of these devices being either analog or digital. The radiation detectors are triggered by the arrival of visible photons and output the primary trigger events to a data acquisition system 804, which obtains a sequence of primary trigger event timings. The timings may be determined in various ways depending on the implementation, for example, in the case of a digital silicon photodiode, a digital timestamp from an avalanche, or for other types of sensors, on a leading-edge threshold triggering, or a constant-fraction discriminator triggering, or an avalanche detection, or other suitable means for detecting the arrival of an ensable of visiblephotons. The primary event trigger timings are output by data acquisition system 804 to be processed by processor 810. Computer-readable medium 806 comprises instructions 808, which processor 810 executes to determine weights for each of the primary trigger event timings, the first primary trigger event timing in the sequence having the largest weight. In particular embodiments, the weights decrease for each subsequent primary trigger event timing in the sequence. In particular embodiments, where the sequence contains at least three primary trigger event timings, then the weight for the last primary trigger event timing will be greater than the weight for at least one other primary trigger event timing in the sequence, in order to compensate for the effect of cutting the sequence off at that point. The onset of a gamma interaction is determined based on at least an overall event trigger timing, which is based on a weighted combination of the primary trigger event timings and their corresponding weights. The onset of the gamma interaction may be output to a suitable imaging system 812. Imaging system 812 may use the onset of the gamma interaction to reconstruct a three-dimensional distribution of the positron-emitting radionuclide within the patient and display a useful image to the doctor or operator.

Figure 9:
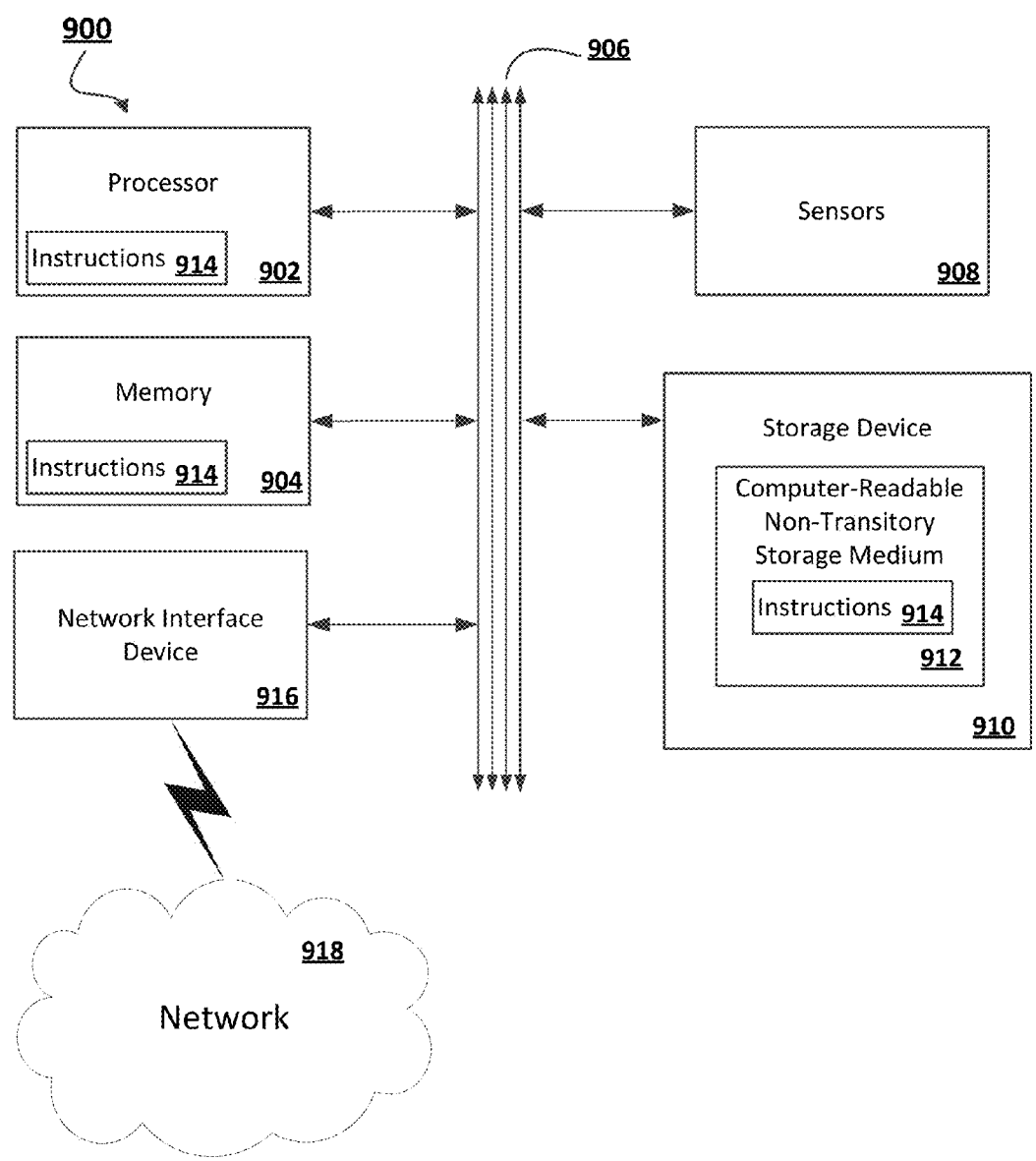
FIG. 9 is a schematic illustrating a computer system adapted to implement the methods and processes described herein.

FIG. 9 illustrates schematically another exemplary embodiment of the invention, comprising a computer system 900 for executing a set of instructions that, when executed, can cause the computer system to perform the processes described above. The computer system 900 can be connected to other computing devices, for example, using a network. In a network, computer system 900 can function in either a server or client capacity, or as a peer machine in a peer-to-peer/distributed network.

The machine can comprise various types of devices, including a personal computer (PC), a server computer, a desktop computer, a laptop computer, a tablet PC, a network router/bridge, or any device capable of executing instructions that specify actions to be taken by the device. While a single device is illustrated, the phrase "computer system" includes any collection of computing devices that execute a set of instructions (individually or jointly) to perform any of the methods and processes described in the present disclosure.

Computer system 900 can include a processor 902 and a memory 904 which communicate together via a bus 906. Computer system 900 can include, for example, sensor inputs 908 (e.g., photosensors, such as PMTs or SiPDs), a storage device 910 (such as a disk drive or optical drive), and a network interface device 916.

Storage device 910 can include a computer-readable non-transitory storage medium 912 which stores one or more sets of instructions 914 operable to implement one or more of the processes described in the present disclosure. Instructions 914 can also be stored within the processor 902 or the memory 904, completely or partially. Computer system 900 can communicate over a network 918, using network interface device 916, and can also send or receive instructions 914 over the network 918. The network 918 may be, for example, a packet switched network using protocols such as TCP/IP, HTTP, etc. Network 918 may also represent any other suitable form of communication between devices, modules, or computer systems, such as USB, PCI, SPI, I2C, or other standards or protocols having the same functions, which may be considered equivalents.

According to one contemplated embodiment, the processes described are performed by the computer system 900, in response to the processor 902 executing an arrangement of instructions contained in the memory 904.

Such instructions can be read into memory 904 from another computer-readable medium, such as storage device 910. Execution of the arrangement of instructions contained in memory 904 causes the processor 902 to perform the process steps described herein. One or more processors in a multi-processing arrangement may also be employed to execute the instructions contained in memory 904. In alternative embodiments, hard-wired circuitry may be used in place of or in combination with software instructions to implement the various embodiments. Thus, the exemplary embodiments are not limited to any specific combination of hardware circuitry and software.

The computer system 900 also includes a network interface device 916 coupled to bus 906. The network interface device 916 provides a two-way data communication coupling to a network 918. For example, the network interface device 916 may be a digital subscriber line (DSL) card or modem, an integrated services digital network (ISDN) card, a cable modem, a telephone modem, or any other interface device to provide a data communication connection to a corresponding type of communication line. As another example, network interface device 916 may be a local area network (LAN) card (e.g., for Ethernet or an Asynchronous Transfer Mode (ATM) network) to provide a data communication connection to a compatible LAN. Wireless links can also be implemented. In any such implementation, network interface device 916 sends and receives electrical, electromagnetic, or optical signals that carry digital data streams representing various types of information. Further, the network interface device 916 can include peripheral interface devices, such as a Universal Serial Bus (USB) interface, a PCMCIA (Personal Computer Memory Card International Association) interface, etc. Although a single network interface device 916 is depicted in FIG. 9, multiple network interface devices can also be employed.

The network interface device 916 typically provides data communication through one or more networks to other data devices. For example, the network interface device 916 may provide a connection through network 918, which may be a local network (LAN), a wide area network (WAN), or the global packet data communication network commonly referred to as the "Internet"), or to data equipment operated by a service provider. The network 918 uses electrical, electromagnetic, or optical signals to convey information and instructions.

The computer system 900 can send messages and receive data, including program code, through the network 918, the network interface card 916, and the bus 906. In the Internet example, a server (not shown) might transmit requested code belonging to an application program for implementing an exemplary embodiment through the network 918, and the network interface device 916. The processor 902 may execute the transmitted code while being received and/or store the code in the storage device 910, or other non-volatile or volatile storage for later execution. In this manner, the computer system 900 may obtain application code in the form of a carrier wave.

Many physical implementations of computer system 900 are possible, including software, hardware (e.g., general processor, Digital Signal Processing (DSP) chip, an Application Specific Integrated Circuit (ASIC), Field Programmable Gate Arrays (FPGAs), etc.), firmware, or a combination thereof, constructed to implement the methods and processes described herein. Computer system 900 may also be embedded in a variety of electronic/computer systems, or may coordinate with one or more modules or devices in other electronic/computer systems to implement the methods and processes described herein. The methods and processes described herein can also be stored as software on a computer-readable non-transitory storage medium and run on a computer processor.

The term "computer-readable non-transitory storage medium" as used herein refers to any medium that participates in providing instructions to the processor 902 for execution. Such a medium may take many forms, including but not limited to non-volatile media and volatile media. Non-volatile media include, for example, optical or magnetic disks, such as the storage device 910. Volatile media include dynamic memory, such as memory 904. Common forms of computer-readable non-transitory storage media include, for example, a floppy disk, a flexible disk, hard disk, magnetic tape, any other magnetic medium, a CD-ROM, CD-RW, DVD, any other optical medium, punch cards, paper tape, optical mark sheets, any other physical medium with patterns of holes or other optically recognizable indicia, a RAM, a PROM, an EPROM, a FLASH-EPROM, any other memory chip or cartridge, or any other medium from which a computer can read.

Various forms of computer-readable non-transitory storage media may be involved in providing instructions to a processor for execution. For example, the instructions for carrying out various embodiments may initially be borne on a magnetic disk of a remote computer. In such a scenario, the remote computer loads the instructions into main memory and sends the instructions over a telephone line using a modem. A modem of the local computer system receives the data on the telephone line and uses an infrared transmitter to convert the data to an infrared signal and transmit the infrared signal to a portable computing device, such as a personal digital assistant (PDA) or a laptop. An infrared detector on the portable computing device receives the information and instructions borne by the infrared signal and places the data on a bus. The bus conveys the data to main memory, from which a processor retrieves and executes the instructions. The instructions received by main memory can optionally be stored on a storage device either before or after execution by the processor.

While the invention has been described in connection with a number of embodiments and implementations, it should be understood that the detailed description and the specific examples, while indicating specific embodiments of the disclosure, are given by way of illustration only, since various changes, modifications, and equivalents within the spirit and scope of the disclosure will become apparent to those skilled in the art from this detailed description.

What is claimed is:

1. A method for detecting the onset of a gamma interaction in a positron emission tomography (PET) imaging system, comprising:
    obtaining a sequence of a plurality of primary trigger event timings;
    applying a predetermined weighting factor to each of the plurality of primary trigger event timings to obtain a sequence of weighted primary trigger event timings;
    combining said sequence of weighted primary trigger event timings to obtain an overall event trigger timing; and
    determining the onset of a gamma interaction in said PET imaging system based at least on said overall event trigger timing.

2. The method of claim 1, wherein the weighting factors for each subsequent primary trigger event timing in the sequence decrease with respect to a previous weighting factor in the sequence.

3. The method of claim 1, wherein the weighting factor for the last primary trigger event timing in the sequence is greater than the weighting factor for at least one other primary trigger event timing in the sequence.

4. The method of claim 1, wherein the combination is a weighted linear combination.

5. The method of claim 1, wherein the number of primary trigger event timings in said sequence is at least three.

6. The method of claim 1, further comprising evaluating the time resolution of the overall event trigger timing, and iteratively modifying at least one of the weighting factors until the time resolution achieves a predetermined threshold value.

7. The method of claim 1, wherein said predetermined weighting factors are determined by:
    evaluating the time resolution of the overall event trigger timing for a plurality of test weights based at least on an analysis of at least one of a numerical simulation of gamma interaction in the system or experimental data regarding gamma interaction in the system; and
    determining a weight for each of the plurality of primary trigger event timings based at least on a test weight from the analysis.

8. A positron emission tomography (PET) imaging system, comprising:
   a data acquisition system operable to obtain a sequence of a plurality of primary trigger event timings;
   a processor; and
   a non-transitory computer-readable medium comprising instructions executed by the processor to:
   apply a predetermined weighting factor to each of the plurality of primary trigger event timings to obtain a sequence of weighted primary trigger event timings;
   combine said sequence of weighted primary trigger event timings to obtain an overall event trigger timing; and
   determine the onset of a gamma interaction in said PET imaging system based at least on said overall event trigger timing.

9. The system of claim 8, wherein the weighting factors for each subsequent primary trigger event timing in the sequence decrease with respect to a previous weighting factor in the sequence.

10. The system of claim 8, wherein the weighting factor for the last primary trigger event timing in the sequence is greater than the weighting factor for at least one other primary trigger event timing in the sequence.

11. The system of claim 8, wherein the combination is a weighted linear combination.

12. The system of claim 8, wherein the number of primary trigger event timings in said sequence is at least three.

13. The system of claim 8, further comprising instructions for evaluating the time resolution of the overall event trigger timing, and iteratively modifying at least one of the weighting factors until the time resolution achieves a predetermined threshold value.

14. The system of claim 8, wherein said predetermined weighting factors are determined by:
   evaluating the time resolution of the overall event trigger timing for a plurality of test weights based at least on an analysis of at least one of a numerical simulation of gamma interaction in the system or experimental data regarding gamma interaction in the system; and determining a weight for each of the plurality of primary trigger event timings based at least on a test weight from the analysis.

15. A non-transitory computer-readable storage medium storing computer-executable program instructions for:
   obtaining a sequence of a plurality of primary trigger event timings associated with a positron emission tomography (PET) imaging system;
   determining a weight for each of the plurality of primary trigger event timings based on predetermined criteria;
   determining the onset of a gamma interaction in the system based at least on an overall event trigger timing, wherein the overall event trigger timing is based at least on a weighted combination of the plurality of primary trigger event timings weighted with corresponding determined weights.

16. The storage medium of claim 15, wherein the weighting factors for each subsequent primary trigger event timing in the sequence decrease with respect to a previous weighting factor in the sequence.

17. The storage medium of claim 15, wherein the weighting factor for the last primary trigger event timing in the sequence is greater than the weighting factor for at least one other primary trigger event timing in the sequence.

18. The storage medium of claim 15, wherein the combination is a weighted linear combination.

19. The storage medium of claim 15, wherein the number of primary trigger event timings in said sequence is at least three.

20. The storage medium of claim 15, further comprising instructions for evaluating the time resolution of the overall event trigger timing, and iteratively modifying at least one of the weighting factors until the time resolution achieves a predetermined threshold value.

21. The storage medium of claim 15, wherein said predetermined weighting factors are determined by:
   evaluating the time resolution of the overall event trigger timing for a plurality of test weights based at least on an analysis of at least one of a numerical simulation of gamma interaction in the system or experimental data regarding gamma interaction in the system; and determining a weight for each of the plurality of primary trigger event timings based at least on a test weight from the analysis.

* * * * *